United States Patent [19]

Miller et al.

[11] Patent Number: 4,505,128
[45] Date of Patent: Mar. 19, 1985

[54] COMPRESSOR SYSTEM FOR DISCHARGING DRY AIR

[75] Inventors: Gregory R. Miller; Steven G. Clark, both of St. Louis County, Mo.

[73] Assignee: Bio-Care Incorporated, St. Louis County, Mo.

[21] Appl. No.: 521,095

[22] Filed: Aug. 8, 1983

[51] Int. Cl.³ .................................................. F25D 21/00
[52] U.S. Cl. .......................................... 62/272; 62/93
[58] Field of Search ............... 62/93, 272, 54, 86, 62/87, 88

[56] References Cited

U.S. PATENT DOCUMENTS

| | | | |
|---|---|---|---|
| 3,091,097 | 5/1963 | Friant | 62/93 |
| 3,226,948 | 1/1966 | Alderson et al. | 62/93 |
| 3,714,790 | 2/1973 | Battey | 62/54 |
| 3,739,594 | 6/1973 | Freese | 62/93 |
| 3,885,394 | 5/1975 | Witt et al. | 62/54 |

Primary Examiner—Ronald C. Capossela
Attorney, Agent, or Firm—Paul M. Denk

[57] ABSTRACT

A compressor system is disclosed for the intake of ambient air having a given amount of moisture or water vapor therein. A compressor compresses the ambient air to a superatmospheric pressure level. The pressurized air discharged from the compressor is run through an intercooler so as to reduce both the temperature of the compressed air and the water vapor therein. The reduced water vapor (i.e., dry) air is then supplied to various respiratory health care apparatus and excess dry air is returned to the inlet of the compressor.

1 Claim, 1 Drawing Figure

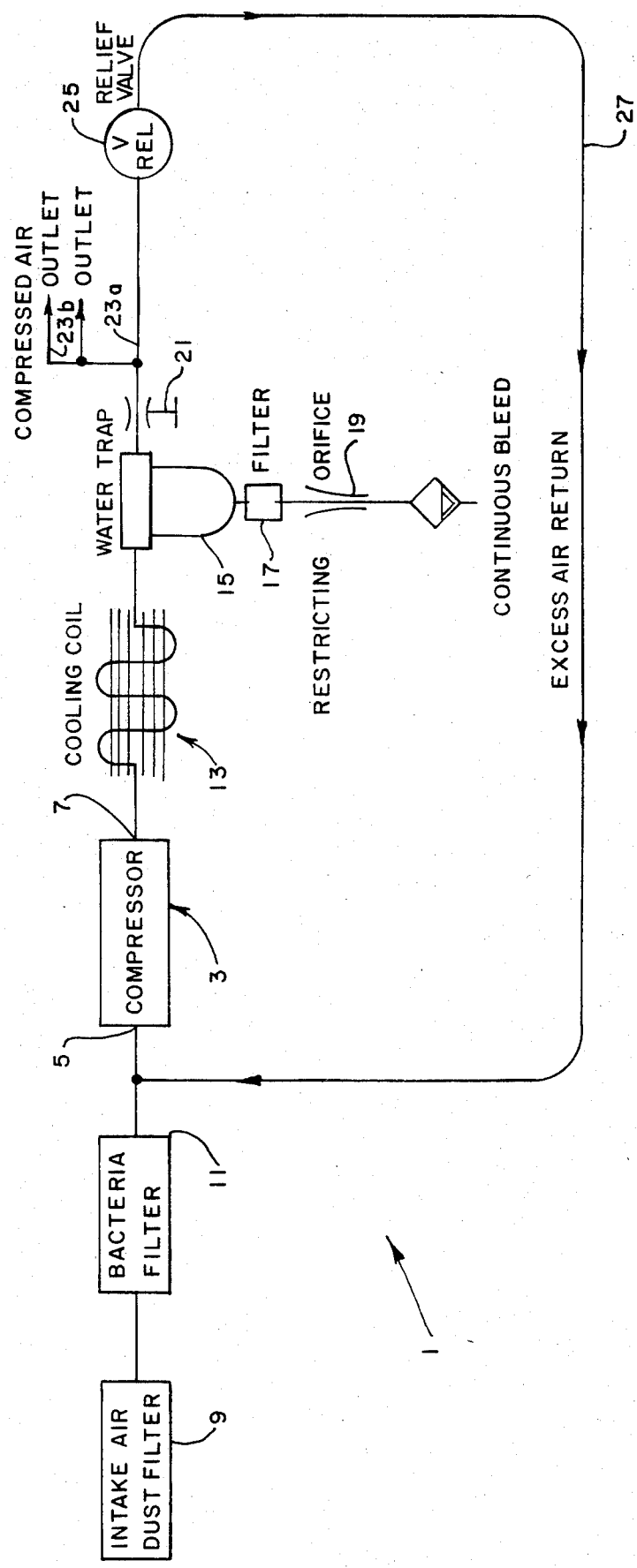

COMPRESSOR SYSTEM FOR DISCHARGING DRY AIR

BACKGROUND OF THE INVENTION

This invention relates to a compressor system for discharging dry (i.e., reduced water vapor) air therefrom, and more particularly to a compressor system for continuously supplying dry air for a variety of respiratory health care equipment, such as aerosol nebulizers, IPPB machines, patient ventilators, and other common respiratory care equipment which require essentially condensation-free superatmospheric air for optimum operation.

Conventionally, the air supply for such respiratory health care equipment includes a compressor which intakes ambient air and compresses it to a superatmospheric pressure level. A water trap is provided to remove condensate from the superatmospheric air before it is discharged to the respiratory health care equipment. However, in practice, it has been found that conventional air compressor systems did not effectively remove condensate under a variety of operating conditions, particularly during humid, hot weather.

It has long been recognized that lowering the amount of water vapor (i.e., lowering the dew point) in the air discharged from an air compressor system for respiratory health care equipment was advantageous in that the potential for damage to the health care equipment could be significantly minimized.

SUMMARY OF THE INVENTION

Among the several objects and features of this invention may be noted the provision of a compressor system for continuously discharging dry air having a dew point significantly below the dew point of the ambient air;

The provision of such a system which recirculates dry, compressed bypassed air past the inlet of the compressor for reducing the quantity of water vapor handled by the system;

The provision of a system which provides a continuous supply of dry air, and yet does not require the use of refrigeration or chemical desiccants; and The provision of such a compressor system which has a long service life, which requires little energy to operate, which is quiet in operation, and which continuously supplies adequate volumes of air at desired pressure levels.

Other objects and features of this invention will be in part apparent and in part pointed out hereinafter.

Briefly stated, an air compressor system of the present invention discharges a supply of superatmospheric air having a relatively low dew point (as compared to the ambient air taken into the compressor). More specifically, the system comprises an air compressor having an inlet and an outlet with the compressor elevating atmospheric air to a superatmospheric pressure level and to an elevated temperature level. An intercooler is provided which receives the superatmospheric air for transferring heat therefrom to the surroundings. Means is provided which receives the cooled superatmospheric air from the intercooler and removes condensed water vapor therefrom and continuously discharges the condensed water to the atmosphere. One or more outlets downstream from the water removal means is provided for discharging compressed air having the desired relatively low dew point (i.e., dry) air. Relief valve means is provided for venting the superatmospheric air in the event it exceeds a predetermined pressure level. Further, means is provided for returning excess low dew point compressed air not discharged from the stated outlets back to the inlet of the compressor whereby the relatively low dew point air is mixed with atmospheric air drawn into the compressor.

BRIEF DESCRIPTION OF THE DRAWING

The FIGURE is a diagrammatic view of the air compressor system of the present invention.

Corresponding reference characters indicate corresponding parts throughout the several views of the drawing.

DESCRIPTION OF A PREFERRED EMBODIMENT

Referring now to the drawing, an air compressor system of the present invention, indicated in its entirety by reference character 1, is shown to continuously discharge a supply of superatmospheric dry air having a relatively low dew point, as compared to the dew point level of the ambient, atmospheric air. More specifically, compressor system 1 includes an electrically driven, continuously operable air compressor 3 having an inlet 5 and an outlet 7. For example, compressor 3 may be a one-half horsepower compressor capable of continuously supplying superatmospheric air at any desired elevated pressure level between about 10 PSIG and 70 PSIG with an output of about 50 liters of compressed air per minute. Such a compressor is commercially available from Thomas Industries, of Sheboygan, Wis., and designated as Model No. 1007CE60. An air intake dust filter 9 and a conventional bacteria filter 11 are provided on the inlet side of compressor 3 for filtering atmospheric air drawn into the compressor.

Those skilled in the art will recognize that the air discharged from outlet 7 of compressor 3 is at a superatmospheric pressure (e.g., 50–70 PSIG). Also, as a consequence of compressing the air, the temperature of the air will have been increased a considerable amount, depending on the operating characteristics of compressor 3.

In accordance with this invention, an intercooler 13 is connected to compressor outlet 7 for receiving the superatmospheric, elevated temperature air and for transferring heat from the superatmospheric air to the surroundings (i.e., to the air within the room). As the superatmospheric air is cooled within intercooler 13, water vapor contained in the superatmospheric air will be caused to at least partially condense, while the working pressure is maintained at a desired pressure level (e.g., 65–70 PSIG). The cooled, superatmospheric air discharged from intercooler 13 then enters a water trap 15 which removes condensate (i.e., the condensed water) from the cooled, superatmospheric air. The water collected in water trap 15 is discharged to the atmosphere after passing through a filter 17 and through a discharge metering orifice 19 such that there is a continuous bleed of the liquid water to the atmosphere. It will be appreciated that the diameter of restricting orifice 19 may be relatively small (e.g., about 0.00001–0.005) inch so as to permit the water to be continuously exhausted therefrom substantially without the discharge or loss of pressurized air. It will further be understood that as the liquid water is discharged from water trap 15, the released condensate may be collected in an evaporator pan (not shown) which may in turn be in heat transfer relation with a portion of compressor 3 or in heat transfer relation with intercooler 13 such that the heat generated by the compressor or by the intercooler may be utilized to evaporate the discharged condensate, thus eliminating the necessity of having a condensate collection tank which would require periodic emptying.

Downstream from water trap 15, an adjustable restricting orifice 21 is provided so as to maintain the working pressure of the cooled, compressed air within the intercooler at about 65–70 PSIG. Downstream from restricting orifice or needle valve 21, a plurality of outlets 23a, 23b are provided which continuously supply dry, compressed air from the compressor system of this invention to desired respiratory health care apparatus (not shown). A pressure relief valve 25 prevents the pressure of the air discharged via outlets 23a, 23b from exceeding a predetermined pressure level (e.g., 50 PSIG). Thus, in essence, the working pressure of the air upstream from restricting orifice 21 is maintained at about 65–70 PSIG, while the pressure downstream from restricting orifice 21 the pressure is maintained at about 50 PSIG.

Further in accordance with this invention, the output capacity of compressor system 1 may exceed the requirements of the respiratory health care apparatus connected to outlets 23a, 23b, and in that event, the dry, compressed air bypassing the outlets is returned to the inlet side of compressor 3 via an excess air return line 27 so as to be mixed with incoming ambient atmospheric air. This mixing of the dry, atmospheric air with the incoming ambient atmospheric air tends to significantly reduce the amount of water vapor drawn through the compressor 3, condensed in cooling coil 13 (i.e., the intercooler) and discharged via water trap 15. This bypass feature thus reduces the amount of water the compressor must handle while assuring that adequate output flow rates are maintained without the requirement of a reservoir tank. By eliminating the requirement of a reservoir, the problem of unwanted condensation in the reservoir is also eliminated. Of course, if the demand of the respiratory health care apparatus equals the output capacity of compressor 3, very little if any excess air will be returned by line 27 and the system of this invention will continue to supply superatmospheric, depressed dew point air to outlets 23a, 23b.

The compressor system 1 of the present invention produces a continuous supply of dry, superatmospheric air having a dew point significantly lower than the dew point of the ambient atmospheric air and yet does not require the provision of any refrigeration system or desiccants used to depress the dew point of the compressed air.

In view of the above, it will be seen that the other objects of this invention are achieved and other advantageous results obtained.

As various changes could be made in the above constructions without departing from the scope of the invention, it is intended that all matter contained in the above description or shown in the accompanying drawing shall be interpreted as illustrative are not in a limiting sense.

What is claimed is:

1. An air compressor system for discharging a supply of superatmospheric air having a relatively low dew point to health care instruments, said system comprising a compressor having an inlet and an outlet, dust and bacteria filter means coupled to the inlet side of the compressor to remove any impurities from the incoming air, said compressor being an approximately one-half horsepower compressor and elevating atmospheric air to a superatmospheric pressure level of between about 50 to 70 PSIG and at an elevated temperature level, intercooling means receiving said superatmospheric air from said compressor for transferring heat therefrom to the surroundings, water trap means receiving said cooled superatmospheric air from said intercooler means for removing condensed water vapor therefrom, discharge metering orifice means connected with the water trap means for continuously discharging the condensed water vapor without any substantial loss of pressurized air therefrom, restricting orifice means connecting downstream with the water trap means to maintain the superatmospheric pressure of the air upstream thereof at approximately about 65 to 70 PSIG, while maintaining the pressure downstream from said restricting orifice means at about 50 PSIG, one or more outlets downstream from said restricting orifice means for discharging compressed air having a relatively low dew point and at approximately 50 PSIG to the health care instruments, relief valve means connecting downstream from the outlets for venting said superatmospheric air in the event that it exceeds approximately 50 PSIG, and means for returning excess low dew point compressed air not discharged from the outlets back to the inlet of the compressor whereby said relatively low dew point air is intermixed with atmospheric air drawn into said compressor.

* * * * *